United States Patent [19]

Miller

[11] Patent Number: 5,340,540
[45] Date of Patent: Aug. 23, 1994

[54] CAP RAISING MECHANISM FOR AN INCUBATOR

[75] Inventor: James G. Miller, Hilton, N.Y.

[73] Assignee: Eastman Kodak Company, Rochester, N.Y.

[21] Appl. No.: 56,637

[22] Filed: May 3, 1993

[51] Int. Cl.$^5$ .................. G01N 31/00; B01L 11/00
[52] U.S. Cl. .................................. 422/64; 422/63; 422/100
[58] Field of Search ............ 422/63, 64, 65, 66, 422/99, 104; 436/46, 48

[56] References Cited

U.S. PATENT DOCUMENTS

| | | | |
|---|---|---|---|
| 4,298,571 | 11/1981 | DeFulvio et al. | 422/65 |
| 4,963,333 | 10/1990 | Shaw et al. | 422/99 |
| 5,034,191 | 7/1991 | Porte | 422/64 |
| 5,059,393 | 10/1991 | Quenin et al. | 422/64 |
| 5,075,079 | 12/1991 | Kerr et al. | 422/64 |
| 5,174,960 | 12/1992 | Shaw et al. | 422/63 |
| 5,192,506 | 3/1993 | Kureshy et al. | 422/64 |

Primary Examiner—Robert J. Warden
Assistant Examiner—Robert Carpenter
Attorney, Agent, or Firm—Dana M. Schmidt

[57] ABSTRACT

An analyzer incubator is provided in which evaporation caps have feet extending through a support on which the caps and covered test elements rest. A preferably fixed mechanism is provided underneath the support to raise and cover both sides of each cap simultaneously to avoid any significant sideways thrust on the cap or on a test element underneath. The cap preferably has downwardly depending feet positioned to cooperate with this mechanism, through the support.

5 Claims, 4 Drawing Sheets

CAP RAISING MECHANISM FOR AN INCUBATOR

FIELD OF THE INVENTION

This invention relates to incubators used in clinical analyzers, and especially to the evaporation caps used therein and the mechanism for raising and lowering them.

BACKGROUND OF THE INVENTION

Evaporation caps are known for incubator stations on a rotor. Examples are disclosed, e.g., U.S. Pat. No. 4,963,333. The caps so disclosed feature camming feet at two of four corners of the cap, and two pivot feet at the other two corners. A recess is provided in the undersurfaces to accommodate two upwardly projecting liquid drops on a potentiometric slide element. The cap works by pivoting on its two pivot feed due to the camming feet riding up onto an incoming slide, thus clearing the cap undersurface from contact with the upwardly projecting drops.

Such a cap works well when the location of the upwardly projecting drops is adjacent the trailing edge of the slide element, such as is the case on the analyzer available from Eastman Kodak Company under the trademark "Ektachem 250", hereinafter the "E-250". It does not work so well, however, if the slide element is turned 180° so that the upwardly projecting drops are adjacent the leading edge of an incoming slide element. The latter occurs when using a slide distributor such as is found in the analyzer disclosed in U.S. Pat. No. 4,298,571. Distributors are particularly useful when using more than 1 incubator, e.g., as in the "Ektachem 700" TM analyzer also available from Eastman Kodak Co. That distributor receives the slide in the orientation mentioned for the "E-250", and then turns it 180° for insertion into an incubator. Such a distributor is not used on the E-250. The reason why the 180° reversal of the slide renders the described cap less useful is that the resulting nearness of the projecting drops to the pivot edge of the cap necessitates a larger size of the camming feet that is impractical.

However, because a single incubator cannot be made indefinitely large, then such a distributor allows for a higher throughput, using plural incubators, than when it is not used. It would be advantageous to provide a cap that cams upwardly by some mechanism as the potentiometric slide enters with the upwardly-projecting drops adjacent the leading edge. Such camming has to be done with some care, since the upwardly-projecting drops should not be jarred sideways, that is, along the axis connecting them, lest the needed flow of the drops towards each other to form a junction, be disturbed.

It is this need that, prior to this invention, has not been achieved inexpensively, by a design allowing ready access to top removal of the caps for cleaning and the like.

SUMMARY OF THE INVENTION

I have constructed an incubator and evaporation caps which solve the aforementioned problems and needs.

More specifically, in accord with one aspect of the invention, there is provided an incubator comprising a support for a slide test element; first means for moving the support about an axis; an evaporation cap movable up and down relative to the support over a slide element on the support, the cap having opposite ends, a sealing surface between the ends to seal a slide element against evaporation, and at least one leg depending from each end; and second moving means for moving the cap up and down relative to the support. The incubator is improved in that the second moving means is disposed under the support, the legs depend through the support into contact with the second moving means, and the second moving means is shaped vertically to move both of the legs simultaneously up relative to the support, and simultaneously down relative to the support, so that the cap raises and lowers without any significant, sideways thrust on it or on a test element underneath the cap.

In accordance with another aspect of the invention, there is provided an evaporation cap for use in an incubator, comprising a body having a surface for sealing over a test element in which an analyte is detected, and at opposite ends of the body, a plurality of downwardly depending legs, one of the opposite ends having a pair of legs at the corners of the one end and the other of the opposite ends having a leg disposed in between the corners of the other end.

Accordingly, it is an advantageous feature of the invention that an incubator is provided with evaporation caps and means for raising and lowering them without any significant sideways thrust, while still allowing easy access to all the caps for removal.

Other advantageous features will become apparent upon reference to the following "Detailed Description", when read in light of the attached drawings.

DESCRIPTION OF THE PREFERRED EMBODIMENTS

The description that follows is of the invention as used in the preferred embodiments, namely in a single analyzer incubator in which potentiometric slide test elements are incubated while being rotated about an axis. In addition, the invention is useful regardless of the other features of the analyzer apart from the incubator or the number of incubators present, and regardless of the type of test element used or the manner in which they are moved through the incubator, so long as the test elements need an evaporation cap.

Descriptors such as "above", "below", "underneath" and the like refer to orientations of parts as they are used when in their preferred assembled positions.

Figure 1:
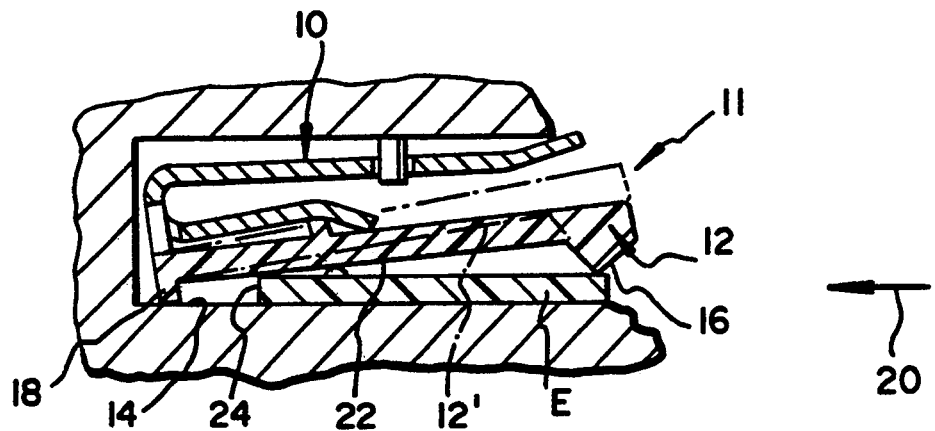
FIG. 1 is an elevational view in section of a prior art evaporation cap, showing its disadvantage when the "wrong" edge of the slide element advances under it.

In FIG. 1, an evaporation cap 12 of the type described in U.S. Pat. No. 4,963,333 is provided at each incubator station 11. Such a cap is biased downwardly by a spring 10 against a support 14 for a slide test element E, for example, potentiometric slide elements available from Eastman Kodak Co. under the trademark "Ektachem" ®. The cap has feet (or legs) 16 and 18 depending at opposite ends, the feet 16 being camming feet that cam the cap upward as a slide element E is inserted, arrow 20. Under-surface 22 between feet 16 and 18 acts to seal the surface of test element E against evaporation. (Additional details can be ascertained from the aforesaid '333 patent.)

The solid line position of cap 12 is very satisfactory, provided the element E is inserted with the liquid drops adjacent the trailing edge (not shown). If instead, as is the case when a distributor (not shown) is used as described above in the "Background", the projecting drops are adjacent the leading edge 24 as shown, then the solid line position of cap 12 is unsatisfactory as it contacts the drop(s). To avoid this, feet 16 would have to be extra large (shown in phantom) to cam the cap up to the position 12' shown. This is an unsatisfactory construct since, among other things, it holds surface 22 too far away to seal element E.

Accordingly, in accord with the invention, the incubator is provided with caps and a cap-raising mechanism, as shown in FIGS. 2-5. Such an incubator comprises an annular test element support ring 30, FIG. 3, on which is located a plurality of individual slide test element supports 32, each defining a station of the incubator. Each station has a width "W" and a length "L" as shown, for example, at support 32'. Supports 32 are recessed between guiding shoulders 34 and 36 used to locate a test element as it is inserted. Ring 30 is preferably mounted on bearings (not shown) and is rotated about axis 38, FIG. 2, by means such as a drive gear 40 and its drive motor (not shown) that engages gear teeth 42 on the inner surface of ring 30.

Figure 3:
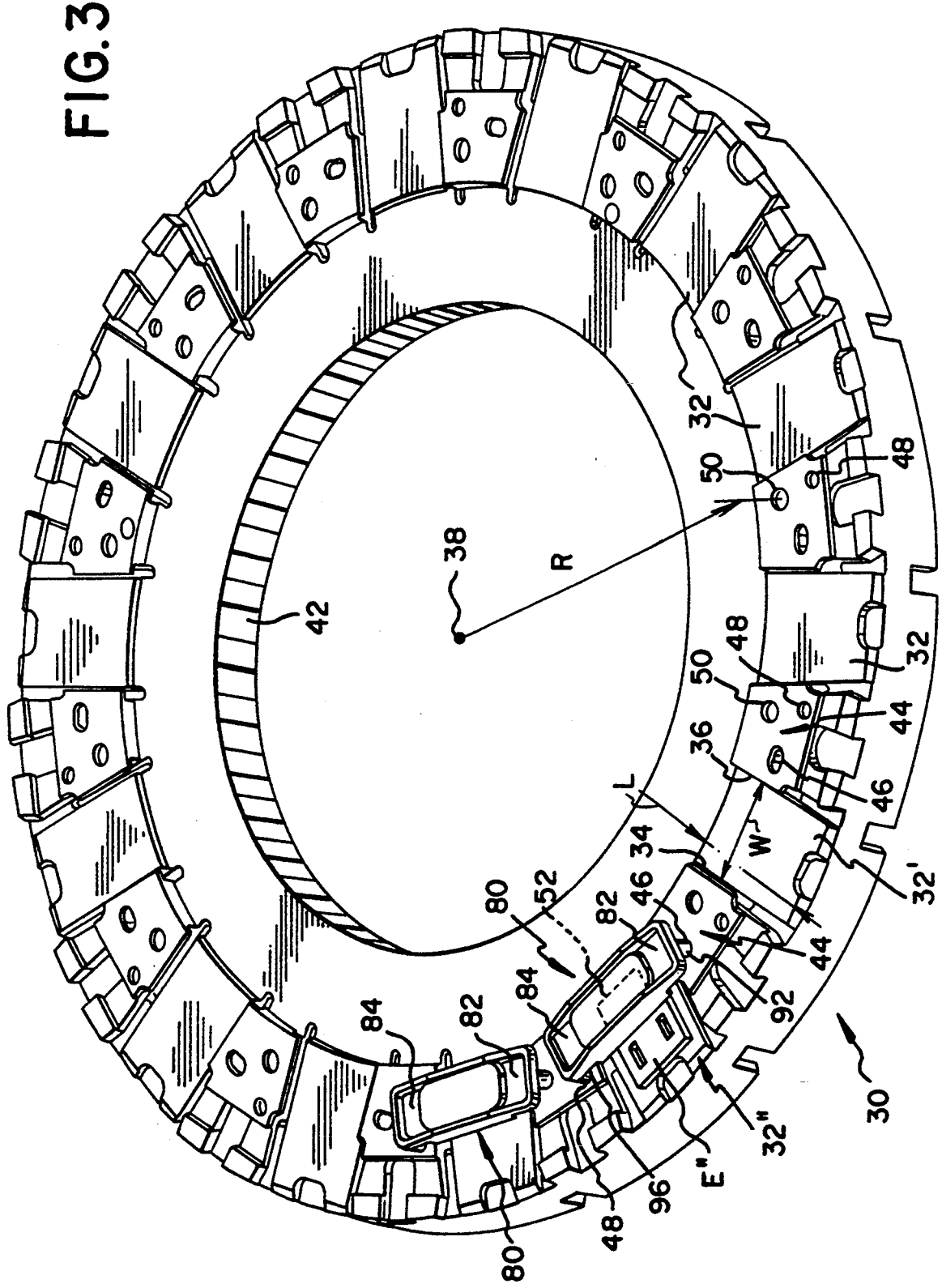
FIG. 3 is an isometric view of the support used in the invention, together with a cap at two of the stations.

Each support 32 is separated from neighboring supports by intervening plates 44, FIG. 3. These in turn are provided at 46, 48, and 50 with 3 apertures extending through ring 30. Apertures 48 and 50 are paired together along a radial direction R of ring 30, and are each offset lengthwise (in the direction of dimension L) from the position of aperture 46, to cooperate with the legs of the cap, discussed below.

Figure 2:
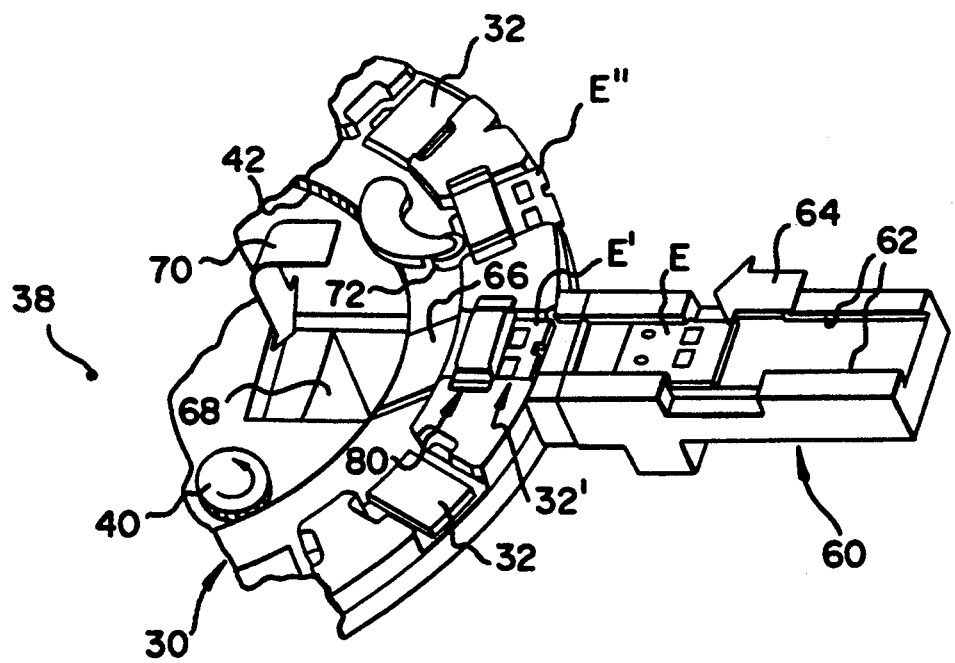
FIG. 2 is a fragmentary isometric view of an incubator, minus its housing, showing the invention.

Loading and unloading of test elements E occurs via a platform 60, FIG. 2, having guide rails 62 through which an element E is pushed, arrow 64, to load the element onto one of the supports 32. To unload a finished element, that is, one already detected elsewhere by a conventional electrometer (not shown), a stationary ramp 66 is provided opposite to platform 60, and is attached, for example, to a dump chute 68 down which an ejected element E is pushed, arrow 70. The pushing is achieved by simply inserting a new slide test element into, e.g., station 32' to eject the "finished" slide test element E' onto ramp 66.

Optionally, a guide roller 72 can be provided to control the amount of insertion of test elements, e.g., element E", as is described more fully in commonly-owned U.S. Pat. No. 5,196,168, issued Mar. 23, 1993, inventors M. Muszak et al., the details of which are expressly incorporated herein by reference.

Figure 4:
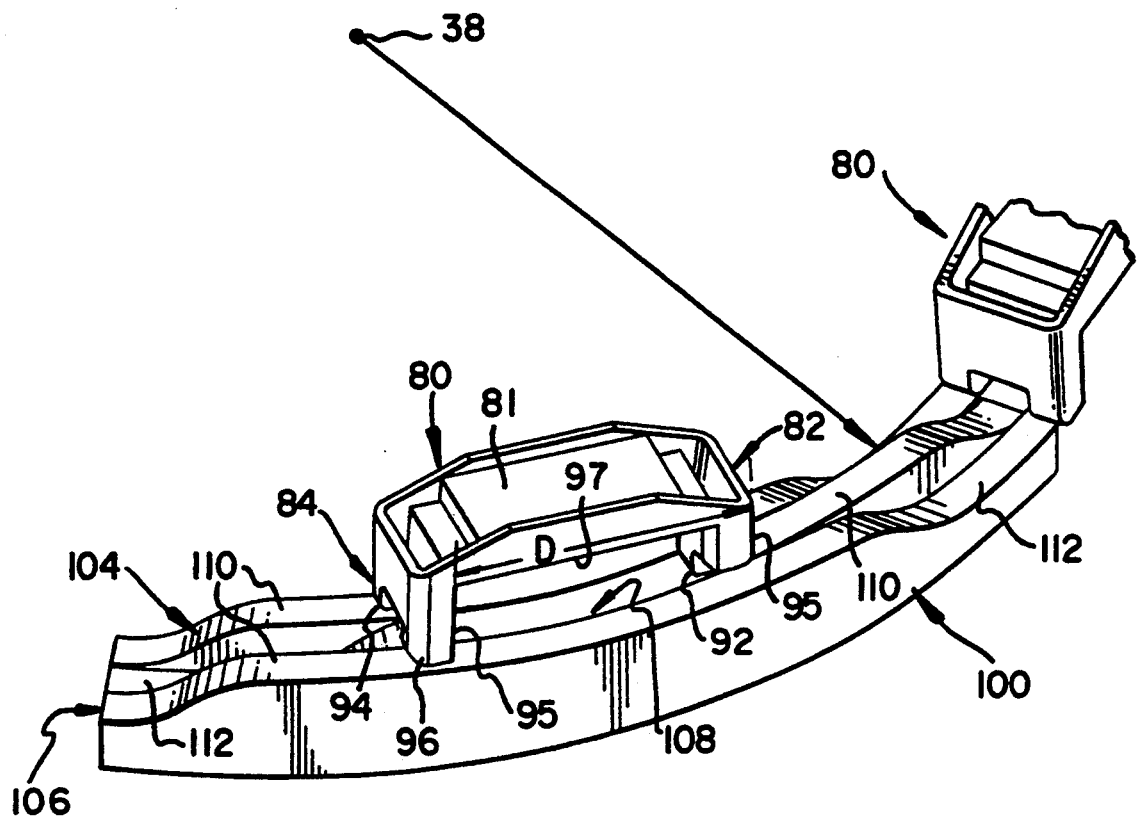
FIG. 4 is an isometric view showing the cooperation between the cap and the cam tracks of the invention, the incubator support having been omitted for clarity.
Figure 5:
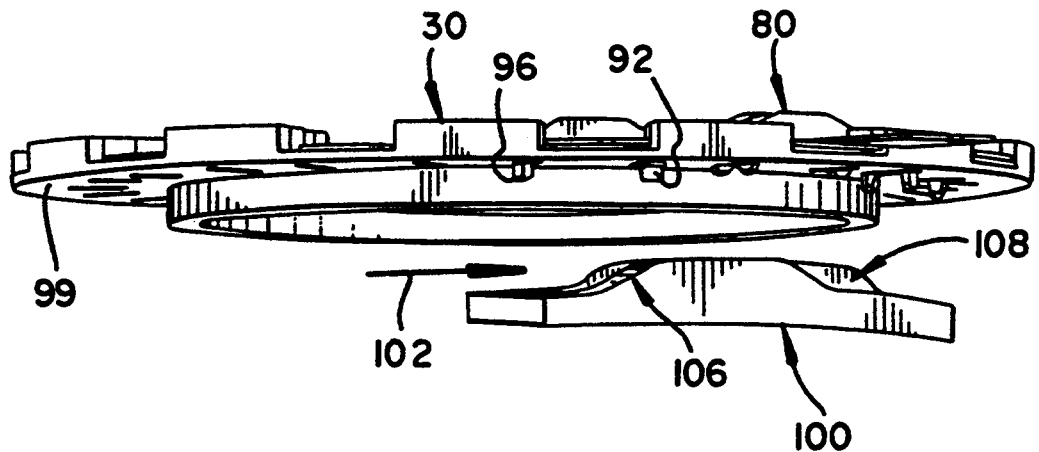
FIG. 5 is an exploded isometric showing all three of the cap, support and cam tracks together.

The evaporation caps 80 are provided as shown more clearly in FIGS. 3-5. More specifically, they comprise a body 81, FIG. 4, having opposite ends 82 and 84, each of which has legs depending therefrom. Most specifically, end 82 has preferably a single leg 92, whereas end 84 has twin legs 94 and 96, offset from each other, and from leg 92, along the length L of each support 32, FIG. 3. The position and size of each leg is such as to loosely extend through its respective aperture in plates 44, as shown in FIG. 5. That is, leg 92 extends through aperture 46, FIG. 3, leg 94 through aperture 50 (not shown) and leg 96 through aperture 48, so that legs 94, 96 (and their apertures) are on one side, and leg 92 and its aperture are on the other side, measured widthwise, of each support 32. Legs 92, 94 and 96 have sufficient length to project substantially below undersurface 99 of ring 30, FIG. 5. The end result is that legs 94 and 96 are located at the corners of end 84, whereas leg 92 is disposed in between the corners of end 82, and preferably, generally at the midpoint between those corners.

Under-surface 97 between leg 92, and legs 94, 96, FIG. 4, acts to seal the drop-containing portion of elements E, using a hollowed-out recess as shown, e.g., in said U.S. Pat. No. 4,963,333, FIG. 2 (and in phantom as recess 52, FIG. 3 herein). The relative position of each cap per its covered test element E" is shown at support 32", FIG. 3.

To ensure that cap end 82 goes up and down substantially simultaneously with cap end 84, a cam 100, FIGS. 4 and 5, is provided, shaped to simultaneously raise (or lower) leg 92 at the time legs 94, 96 are raised (or lowered). To ensure nothing is in place above the caps 80 to obstruct access to the caps from above, cam 100 is disposed fixedly underneath ring 30 which rotates above it, arrow 102, FIG. 5. More specifically, cam 100 comprises a cam track 104, 106 and 108 for each of legs 94, 96 and 92, respectively, FIG. 4. Because of the location of legs 92, 94 and 96, each track occupies about ⅓ of the overall surface of cam 100, with track 108 occupying the middle ⅓. Each track also comprises a top land portion 110 and a root portion 112 that is below top land portion 110. Because legs 94 and 96 are radially aligned on ring 30, so are top land portions 110 for tracks 104 and 106. However, the onset of top land portion 110 for track 108, as well as the onset of its root portion 112, is spaced a distance circumferentially about axis 38, from the onset of the respective portions of tracks 104 and 106, that is effective to raise leg 92 (or lower it) at the same time that legs 94 and 96 are raised (or lowered). That spacing distance is of course the distance "D" between the leading edges 95 of a leg 92 and of paired legs 94, 96.

As a result, as ring 30 moves (preferably, rotates) above cam 100, arrow 102, FIG. 5, each cap is caused to raise and lower at the position at which platform 60 and ramp 66 are located, FIG. 2, to allow loading and unloading of a test element, if needed. Because each end of the cap 80, arranged across the width W of each test element support 32 in the direction of travel of ring 30, goes up and down simultaneously as controlled by cam 100, the cap experiences substantially no sidewise thrust (across the width W of supports 32) and hence no significant sideways thrust is delivered to any test element underneath the cap. As used herein, "significant sideways thrust" means any such thrust that generates more than one gravitational force on the fluid mass on the test element.

Thus, the two drops conventionally space apart sideways on a potentiometric test element under the cap are not jolted towards each other such as could render the test inoperative.

Figure 6:
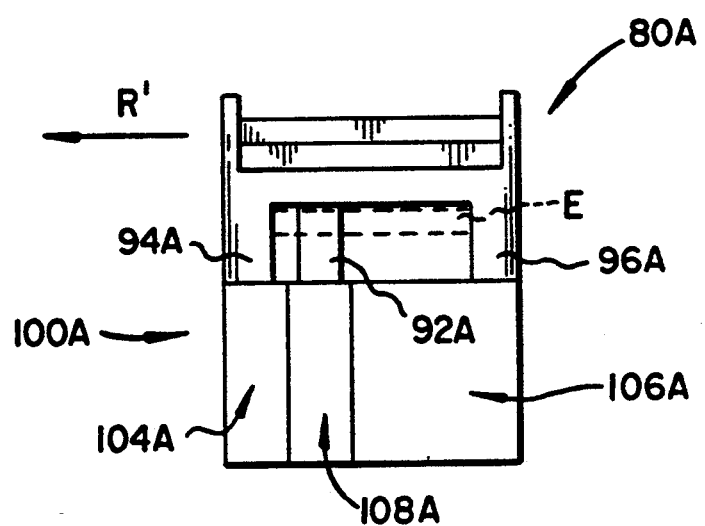
FIG. 6 is an end elevational view of a cap and cam track, minus the incubator support, of an alternate embodiment of the invention.

It is not essential that the single leg of end 82 be at the midpoint of that end. It can, for example, be at any location between the corners of that end, FIG. 6. Parts similar to those previously described bear the same reference numeral, to which the distinguishing suffix "A" is appended. Thus, for the embodiment of FIG. 6, leg 92A of cap 80A is radially (in the direction of "R'") closer to leg 94A than it is to 96A. Similarly, track 106A occupies almost ½ of the volume of cam 100A, and the other tracks 104A and 108A only about 25% each, because of the location of the cap legs. The position of a test element E when sealed by cap 80A is shown in phantom.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In an incubator comprising a support for a slide test element; first means for moving said support about an axis; an evaporation cap movable up and down relative to said support over a slide element on said support, said cap having opposite ends, a sealing surface between said ends to seal a slide element against evaporation, and at least one leg depending from each end; and second moving means for moving said cap up and down relative to said support;

the improvement wherein said support has apertures therethrough and said second moving means is disposed under said support, said legs depending through said support apertures into contact with said second moving means, and said second moving means is shaped to move both of said legs simultaneously up relative to said support, and simultaneously down relative to said support, so that said cap raises and lowers without any significant, sideways thrust on it or on a test element underneath said cap.

2. In an incubator for incubating a test element bearing a biological liquid prior to detecting a signal in the element that is proportional to an amount of an analyte of choice present in the liquid, the incubator comprising at least one station, said at least one station comprising a test element support surface at said at least one station that extends widthwise from opposite sides and an evaporation cap disposed over said support for movement up and down relative to said support to allow insertion and removal of a test element between said support and said cap, said cap including legs projecting downward toward said support, and raising means for raising and lowering said cap relative to said support;

the improvement wherein said at least one station includes through-holes, at least one of which is on either of said sides of said support surface, said through-holes being the same in number and position as said legs on said cap, and wherein said legs project through said through-holes;

and said raising means comprise a camming track underneath said support for each of at least two different ones of said cap legs, said camming tracks having a shape to raise a cap leg on one side of said support while a cap leg on the other side of said support is being raised simultaneously; and moving means for providing relative motion between said support and said camming tracks, so that said cap raises and lowers without any significant, sideways thrust on it or on a test element underneath said cap.

3. An incubator as defined in claim 1, wherein there are three of said cap legs and three of said through-holes, two of each being on one side of said support at said station and the other being on the other side of said support station, and wherein said moving means provides motion in a direction in which one of said sides of said support proceeds the other of said sides.

4. An incubator for incubating a test element bearing a biological liquid prior to detecting a signal in the element that is proportional to an amount of an analyte of choice present in the liquid, the incubator comprising
at least one station, each said at least one station comprising a test element support having a width and length and apertures therethrough,
means for rotating said at least one station about an axis so that said support travels in the direction of its width,
an evaporation cap straddling the width of said support, said cap having a leg depending therefrom through said apertures on either side of said support, one leg being offset along the length of said support from the other leg, said legs extending through said support apertures;
and a cam under said support, said cam having at least two tracks, each offset from the other in the direction of said length of said support by a distance effective to ensure one of said legs but not the other, rides on said each track, each said track further including a top land portion and a root portion, said top land portions being spaced a distance from each other and said root portions being spaced a distance from each other effective to ensure that said cap raises and lowers, respectively, on said tracks at each leg simultaneously,
so that no significant sideways thrust occurs on said cap or on a test element underneath.

5. An incubator as defined in claim 4, wherein said cap has a third leg, two at one end and one at the other, and said cam comprises a track for each leg, the tracks for said two legs at one end of said cap being identical in the positioning of said top land portions and said root portions.

* * * * *